United States Patent [19]
Johansen et al.

[11] 3,972,614
[45] Aug. 3, 1976

[54] METHOD AND APPARATUS FOR MEASURING ONE OR MORE CONSTITUENTS OF A BLOOD SAMPLE

[75] Inventors: Ebbe Johansen, Birkerod; Finn Chresten Lundsgaard, Taastrup, both of Denmark

[73] Assignee: Radiometer A/S, Denmark

[22] Filed: July 10, 1974

[21] Appl. No.: 487,368

[52] U.S. Cl. .......................... 356/36; 259/DIG. 44; 356/39; 356/40; 356/73
[51] Int. Cl.[2] .................. G03B 27/76; G03B 27/52
[58] Field of Search .................. 356/36, 39, 40, 41, 356/73; 73/69; 259/DIG. 44

[56] References Cited
UNITED STATES PATENTS

| | | | |
|---|---|---|---|
| 3,715,104 | 2/1973 | Cottell | 259/DIG. 44 |
| 3,874,850 | 4/1975 | Sorensen et al. | 356/40 |

*Primary Examiner*—Vincent P. McGraw
*Attorney, Agent, or Firm*—Robert E. Burns; Emmanuel J. Lobato; Bruce L. Adams

[57] ABSTRACT

The invention relates to a method and apparatus for measuring one or more data of blood samples, such as oxygen saturation, contents of hemoglobin, bicarbonate, sodium, potassium, etc. involving hemolyzation of the blood sample. The blood sample is passed into a conduit and hemolyzed therein by imparting ultrasonic waves to all parts defining said conduits. Measurement is performed after and possibly also prior to hemolyzation. In its preferred embodiment the apparatus according to the invention comprises a computer for automatically controlling the operational sequence of the components of the apparatus and for receiving measuring signals from measuring devices of the apparatus and converting said signals into immediately understandable digital data.

20 Claims, 4 Drawing Figures

METHOD AND APPARATUS FOR MEASURING ONE OR MORE CONSTITUENTS OF A BLOOD SAMPLE

BACKGROUND OF THE INVENTION

1. Field of the Invention

The present invention relates to a method and apparatus for performing measurement of constituents of blood samples necessitating hemolyzation of said samples. Measurements of that type include determination of oxygen saturation, hemoglobin concentration, erythrocyte electrolyte concentration, etc.

2. Description of the Prior Art

Known apparatuses for measuring the oxygen saturation or hemoglobin concentration in blood samples comprise photometric measuring devices including a light source for emitting light through the blood sample to a photoelectric cell. In order to obtain accurate and reliable measurements it is common practice to hemolyze a blood sample to be measured before introducing it into the apparatus. Such hemolyzation of blood samples was previously normally obtained by cooling them to a temperature below the freezing point or by adding a suitable solvent to the blood samples. It is understood that such separate hemolyzation operation enhances the risk of errors and makes increased demands on the skill of the operator.

In an article entitled "Effects of Hemolysis on Plasma Electrolyte Concentrations of Canine and Porcine Blood" published by Dwight B. Coulter and Larry L. Small in the periodical Cornell Wet. 61 (4), 660, a test has been described wherein a blood sample was divided into two tubes. One of these tubes was exposed to high-frequency sound to produce partial hemolysis, and thereafter the degree of hemolysis and its influence on plasma electrolyte concentrations was determined.

SUMMARY OF THE INVENTION

According to the invention an apparatus for hemolyzing a blood sample and for measuring at least one constituent thereof has been provided, said apparatus comprising a conduit for conducting said blood sample and including a hemolyzing section, means for generating ultra-sonic waves or high-frequency sound in walls defining said hemolyzing section so as to at least partly hemolyze a blood sample contained therein, first means for measuring said constituent on the hemolyzed blood sample, and means for subsequently flushing the blood sample out of said conduit.

The apparatus according to the invention may further comprise second means for concentrations said constituent on the blood sample in said conduit before hemolyzation thereof. In that case said first and second measuring means may comprise electro-chemical measuring devices for measuring electrolyte concentraions (such as sodium, potassium, bicarbonate, etc.) in the blood sample and on the basis of these measurements erythrocyte and plasma electrolyte concentrations in the blood sample may be determined. The electrochemical measuring devices used may be the socalled half-cell electrodes.

The said first and second measuring means may be arranged at positions spaced along said conduits, and the apparatus may further comprise means for moving an unhemolyzed blood sample to said second measuring means and subsequently to said hemolyzing conduit section when the measurement on the unhemolyzed blood sample has been performed. The said first measuring means may be arranged at said hemolyzing conduit section so that measurement by means of said first measuring means may be performed without further movement of the blood sample as soon as the necessary hemolyzation process has been terminated. Alternatively, the said first measuring means may be arranged at a position spaced from said hemolyzing conduit section so that the blood sample has to be moved to that position after hemolyzation. However, more preferably, said first as well as said second measuring means may be arranged at said hemolyzing section so that the measurement before and after the hemolysis in said hemolyzing conduit section may be performed without intermediate moving said blood sample in said conduit.

Instead of or in addition to the determination of electrolyte concentrations the apparatus according to the invention may for example be used for determination of oxygen saturation and/or haemoglobin concentration of a blood sample. For that purpose the apparatus may comprise a photometric measuring device which is preferably — but not necessarily — arranged at the hemolyzing conduit section in order to avoid movement of the blood sample within said conduit after hemolyzation and prior to measurement thereof.

The apparatus according to the invention may comprise electronic means, including computer means, for automatically controlling the operational sequence of the apparatus in timed relationship and for displaying data corresponding to the values measured by said measuring means.

According to another aspect the present invention comprises a method for measuring at least one solute in a sample of whole blood, said method comprising passing the blood sample into a conduit, measuring said solute in a sample of whole blood, thereafter at least partly hemolyzing said blood sample within said conduit by means of ultra-sound, measuring said solute in the hemolyzed blood sample, and subsequently flushing said hemolyzed sample out of said conduit.

BRIEF DESCRIPTION OF THE DRAWING

Embodiments of the apparatus and method according to the invention will now be described more in detail with reference to the drawings wherein.

DESCRIPTION OF THE PREFERRED EMBODIMENTS

Figure 1:
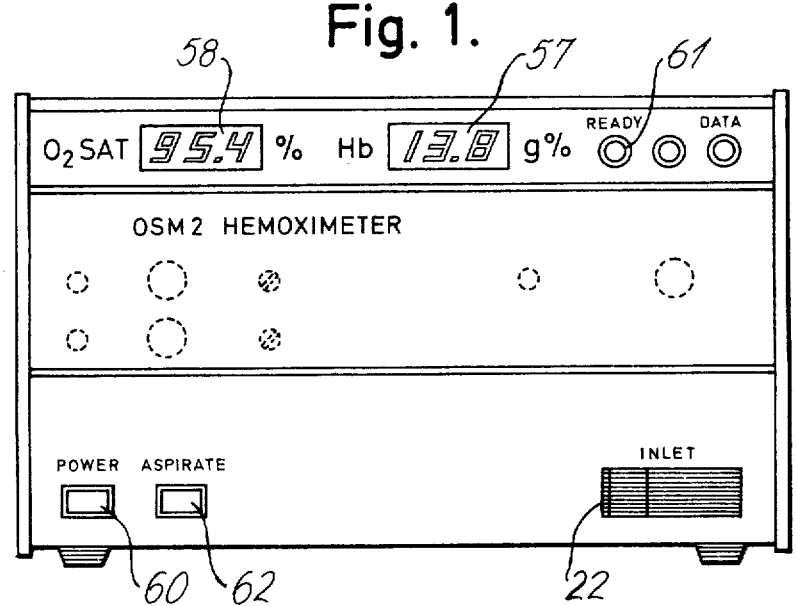
FIG. 1 shows a front view of a first embodiment of the apparatus according to the invention.
Figure 2:
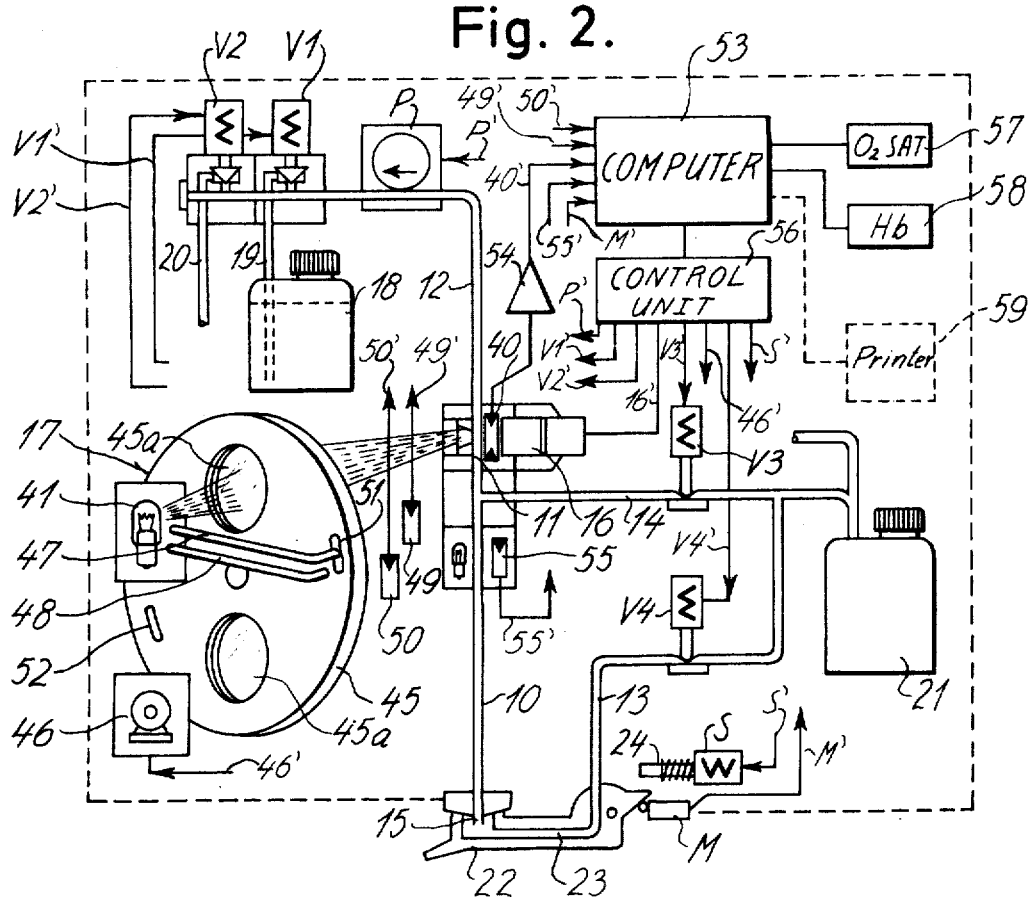
FIG. 2 shows a diagram indicating the various components of the apparatus shown in FIG. 1.
Figure 3:
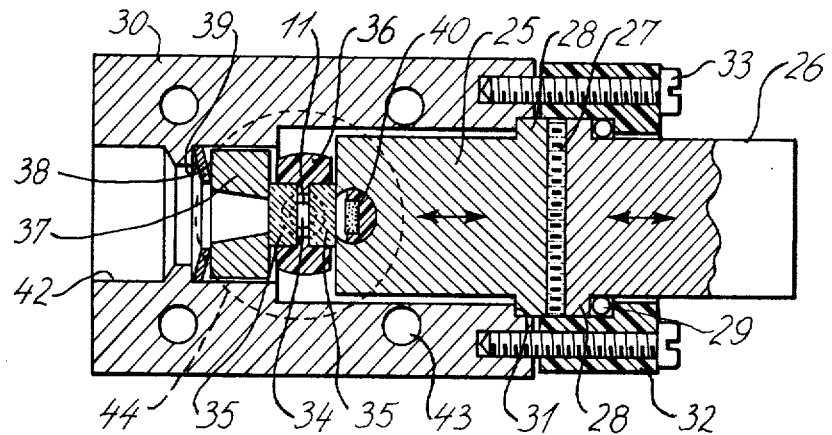
FIG. 3 shows a side view and partially sectional view of a high frequency generator contained in the apparatus illustrated in FIGS. 1 and 2.

The apparatus illustrated in FIGS. 1 – 3 may be used for accurately measuring of oxygen saturation (i.e. the relation between the amount of oxydized hemoglobin and the total amount of oxydized and reduced hemoglobin and/or haemoglobin concentration in a blood sample, and the apparatus is adapted to directly display the measured values. The apparatus contains a fluid conduit system comprising an inlet section 10, a measuring section 11, a rinsing fluid section 12, a shunt conduit section 13, and a drainage conduit section 14. The inlet section 10 has a free end portion 15 extending outwardly from the front panel of the apparatus so that a blood sample may be injected or aspirated into the inlet section 10 through said free end portion. The inlet and measuring sections 10 and 11 are preferably of such a size that a sample of about 20 microlitres blood is sufficient for performing measurements in the apparatus. The measuring section 11 extends through an ultrasonic generator 16 cooperating with a photometric hemoglobin measuring device 17 as described more in detail below. The rinsing fluid section 12 is connected to a rinsing fluid container 18 through a branched conduit 19 which is controlled by a valve V1, and to the atmosphere or another source of rinsing gas (not shown) through a branched conduit 20 which is controlled by a valve V2. A pump P which is preferably of the peristaltic type cooperates with the rinsing fluid section 12 for pumping gas and/or liquid through the fluid conduit system. The drainage conduit section 14 communicates with a waste container 21 and is controlled by a valve V3, and the shunt conduit section 13 which is branched off from the drainage conduit section between the container 21 and the valve V3, is connected to an inlet key 22 and is controlled by a valve V4. The inlet key which is swingably mounted on the front panel of the apparatus has an inner passage 23 communicating at one end with the adjacent flexible end portion of the shunt conduit section 13. The key 22 is movable between a closed position in which the other end of the inner passage 23 surrounds the projecting free end portion 15 of the inlet section 10 and thereby establishes communication between the sections 10 and 13, and an open position in which the communication between the inlet and shunt sections is broken. A microswitch M may be actuated by movement of the key 22, which may be locked in its closed position by means of a locking device 24 actuated by a solenoid S.

The details of the ultra-sonic generator 16 is illustrated in FIG. 3. The said generator comprises a pair of oppositely arranged piston-like blocks 25 and 26 which are preferably made of metal such as brass, and the adjacent end surfaces of the pistons or blocks 25 and 26 are contacting a member of the disc 27 of a piezoelectrical material arranged between said pistons or blocks. The members 25, 26, and 27 constitute an acoustic resonator. Each of the pistons 25 and 26 is provided with a radially extending collar or flange 28 at the end surface abutting the piezoelectrical disc 27, and an electrical conductor member 29, such as a copper wire, surrounds the piston 26 and is in engagement with the flange 28 thereof. The conductor member 29 is electrically connected to an AC voltage generator (not shown). The piston 25 is arranged within a housing 30 of metal, such as aluminum, having an annular shoulder 31 engaging the flange 28 of the piston 25. The flanges 28 of the pistons 25 and 26, the intermediate disc of piezoelectrical material 27, and the conductor member 29 are clamped between the shoulder 31 and a corresponding internal shoulder formed in an annular clamping member 32 which is fastened to the end surface of the housing 30 by means of screws 33 or other suitable fastening means. The clamping member 32 is made from an electrically insulating material, for example a reinforced plastic material which is able to resist the vibrating forces to which it is exposed during operation. It is understood that when an alternating potential difference is provided between the pistons 25 and 26 by means of the voltage generator electrically connected to the piston 26, the pistons 25 and 26 will be vibrated in their axial direction as indicated by arrows in FIG. 3 due to the piezoelectrical effect of the disc 27. The said voltage generator is preferably operated at a frequency corresponding substantially to the resonance frequency of the acoustic resonator formed by the members 25, 26, and 27.

The measuring section 11 of the fluid conduit system in the apparatus shown in FIGS. 1 – 3 of the drawing comprises a measuring chamber 34 defined between a pair of spaced, oppositely arranged, transparent plate members or pane members 35 which is mounted in a frame 36. The frame 36 with the pane members 35 is arranged in the housing 30 between the inner end of the piston 25 and an annular backing member or anvil member 37, and a spring member 38 is arranged between the anvil member 37 and an inner shoulder 39 of the housing to secure that the anvil member and the piston 25 are maintained in close contact with the adjacent outer surfaces of the pane members 35. It should be understood that the measuring section 11 extends transversely to the plane of the drawing in FIG. 3 which consequently shows a cross-section of the measuring chamber 34. The end surface of the piston 25 contacting the adjacent pane member 35 has a recess receiving a photoelectric cell 40 or a similar light sensing device which may provide an electrical signal varying in response to the intensity of light received. The photoelectric cell 40 forms part of the haemoglobin measuring device 17 which also comprises a light source 41 from which light may be transmitted through a bore 42 in the housing 30 and through the spring member 38, the anvil member 37, and the pane members 35 to the photoelectric cell 40. If desired, the bore 42 may be provided with internal threads (not shown) for mounting the measuring device 17 or components thereof. Transverse bores 43 may be defined in the housing 30 for receiving screws, bolts, or similar means for fastening the ultrasonic generator 16 to the frame of the apparatus. In FIG. 3 the dotted line 44 indicates a cylindrical recess for receiving adjacent parts of the apparatus associated with the measuring section 11, and said adjacent parts may comprise suitable means for maintaining the measuring section 11 at a substantially constant temperature. As illustrated in FIG. 2 the hemoglobin measuring device 17 comprises a rotatable disc 45 which may be driven by means of a motor 46. The disc 45 contains diametrically oppositely arranged openings in which two different interference filters 45a are mounted. One of these light filters only transmit green light having a wave length of about 505 nm at which oxyhemoglobin and reduced hemoglobin have an isobestic point, that means a wave length at which the extinction values of oxyhemaglobin and reduced hemoglobin are identical. The other of the light filters 45a only transmits red light having a wave length of about 600 nm, or another wave length where the extinction values of the said two types of hemaglobin differ considerably.

The measuring device 17 also comprises two fiber optical guiding members 47 and 48 or another type of light guides by means of which light from the light source 41 may be transmitted to two selected radially spaced points of the disc 45. Each of the light guiding members 47 and 48 cooperates with photoelectric cells 49 and 50, respectively, or other light sensing means which may receive light from the light source 41 transmitted by the light guiding members through associated openings 51 and 52 in the rotatable disc 45. It is understood that each of the photoelectric cells 49 and 50 receives light from the light source 41 only in one angular position of the disc 45, namely in the position in which the end of the associated light guiding member is registering with the corresponding opening in the disc 45.

A computer 53 may receive signals from the photoelectric cell 40 through a line or conductor 40' which includes an amplifier 54 for amplifying these signals. The computer 53 may also receive signals from the photoelectric cells 49 and 50 through lines or conductors 49' and 50', respectively, and from the microswitch M through a line or conductor M'. A liquid sensing device 55 for sensing the presence or absence of a liquid in the inlet section 10 of the conduit system may comprise a light source and a light sensing device, such as a photoelectric cell, and the light sensing device 55 is also connected to the computer 53 through a conductor or line 55'. The computer cooperates with a control unit 56 adapted to control the function of the valves V1, V2, V3, and V4 through lines or conductors V1', V2', V3', and V4', respectively, and the function of the ultrasonic generator 16, the pump P, and of the solenoid S through lines or conductors 16', P', and S', respectively. The computer 53 is also connected to display devices 57 and 58 and/or to a printer 59.

The function of the apparatus shown in FIGS. 1 – 3 is as follows:

When a POWER-button 60 has been depressed and a READY-lamp 61 on the front panel of the apparatus (FIG. 1) indicates that the apparatus is ready for use the solenoid S is energized and the locking device 24 is in its retracted, non-locking position so that the inlet key 22 may be opened. When the operator moves the inlet key to its opened position the microswitch M is actuated whereby the apparatus is placed in a "ready"- position in which the valve V3 is open whereas the other valves V1, V2, and V4 are closed. A sample of whole blood or of erythrocyte concentrate to be measured may now be injected into the inlet section 10 from a syringe. The blood sample may alternatively be aspirated into the inlet section by means of the pump P. In the latter case the operator depresses the ASPIRATE-button 62 whereby the valve V2 is being opened whereas the valve V3 is being closed, and the pump P is being actuated. When blood injected or aspirated into the inlet section 10 reaches the liquid sensing device 55 this device generates a signal indicating to the computer that a sufficient amount of blood sample has been introduced, and this may for example be indicated to the operator by extinction of the lamp 61. If the operator nevertheless continues injection of blood the excessive amount thereof will flow through the drainage conduit section 14 to the waste container 21. After injection or aspiration of the blood sample the operator moves the inlet key 22 to its closed position whereby the microswitch M generates a signal indicating to the computer that the measuring procedure may be initiated. Thereafter the control unit generates a signal deenergizing the solenoid S so that the locking device 24 is being moved to the position in which the inlet key 22 is locked. Furthermore, the control unit closes the valve V3 whereas the valve V2 is being opened. Now, the pump P is operated to move the blood sample from the inlet section 10 into the measuring section 11. Thereafter the ultrasonic generator 16 is energized whereby the blood sample within the measuring chamber 34 defined between the pane members 35 are exposed to ultrasonic waves, preferably at a frequency of 15 – 100 and more preferred at 20 – 50 kilocycles per second. When the blood within the measuring chamber 34 has been at least partly hemalyzed by the ultrasonic waves the disc 45 is rotated by the motor 46 at a suitable rotational speed, and the filters 45a will alternately pass the light source or lamp 41 and register with the bore 42 in the housing 30 for a short period of time in which the filtered light having a predetermined wave length as described above passes through the transparent pane members and the hemolyzed blood sample therebetween. The photoelectric cell 40 generates a signal being a measure for the optical density of the haemolyzed blood sample for light having the wave length in question. Part of the light emitted from the light source 41 is passed through the light guiding members 47 and 48, and when one of the filters 45a is in register with the photoelectric cell 40 in the ultrasonic generator 16 one of said light guiding members is registering with its associated opening 51 or 52 and the corresponding photoelectric cell 49 or 50. The signal thereby generated by the photoelectric cell 49 or 50 indicates to the computer which one of the filters 45a is passing the lamp 41. It is understood that the computer will receive alternating signals from the photoelectric cell 40 representing measurements of the optical density of the haemolyzed blood sample for two different colours (two different wave lengths) of light, respectively. On the basis of these requirements the oxygen saturation and the contents of haemoglobin in the blood sample may be calculated by the computer 53 on the basis of known principles, and the results may be displayed by the display devices 57 and 58 and/or printed by the printer 59.

After termination of the measuring procedure the rinsing procedure may be initiated. The valves V2 and V4 are now opened, and the pump P is operated so as to pump air or another rinsing gas through the conduit 20, the rinsing fluid section 12, the measuring section 11, the inlet section 10, the inner passage 23 of the inlet key 22, and through the shunt conduit section 13 to the waste container 21. Thereby the blood sample is driven out of the conduit system and into the waste container 21. The valve V2 may now be closed and the valve V1 may be opened so that a rinsing liquid is pumped from the container 18 through the conduit sections 12, 11, 10, 23, and 13 to the container 21. Thereafter the valve V1 may again be closed and the valve V2 may be opened while the pump P is still operating so that the rinsing liquid is flushed out of the conduit system and into the container 21 by rinsing air or gas. If desired, the rinsing procedure may be repeated. When the rinsing procedure has been terminated the solenoid S is energized and the READY-lamp 61 is being turned on to indicate that the apparatus is ready to receive a further blood sample.

Although the operational programme of the apparatus has not been described in detail it will be understood by those skilled in the art that the operational sequence of the various components and parts of the apparatus may be automatically controlled by the computer 53 and its associated control unit 56, for example in a manner similar to that described in assignee's co-pending U.S. patent application Ser. No. 306,661, now U.S. Pat. No. 3,874,850.

Oxygen saturation of blood is dependent on temperature. Therefore, the apparatus should preferably comprise means for maintaining at least the measuring section 11 at a substantially constant temperature, for example about 37°C.

Figure 4:
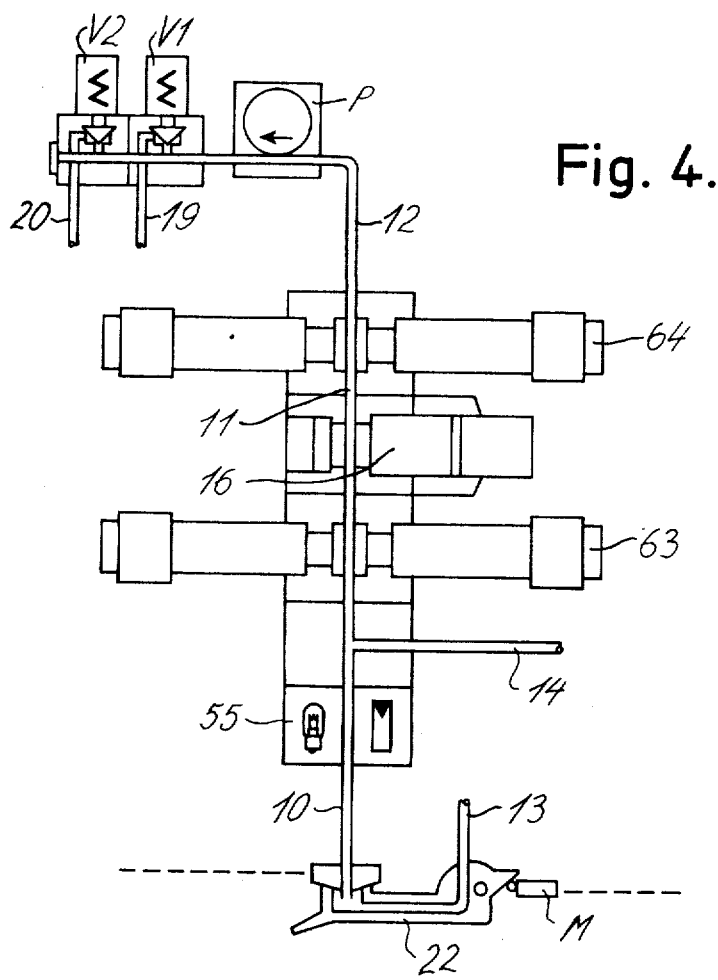
FIG. 4 shows diagrammatically a second embodiment of the apparatus according to the invention.

FIG. 4 shows a modified embodiment of the apparatus adapted for measuring electrolyte concentrations in a blood sample. Components in FIG. 4 similar to those shown in FIGS. 1 – 3 are indicated by similar reference designations. The embodiment shown in FIG. 4 may correspond to that shown in FIGS. 1 – 3 apart from the components associated with the measuring section 11. In FIG. 4 the ultrasonic generator 16 may correspond to that shown in FIG. 3, but has no haemoglobin measuring device 17 associated therewith and therefore the generator 16 does not contain the photoelectric cell 40. The embodiment shown in FIG. 4 comprises instead electrochemical measuring devices 63 and 64, for example the so-called half-cell electrodes being adapted to measure the concentration of a selected electrolyte in the blood sample, such as bicarbonate, sodium, potassium, etc. The measuring device 63 is arranged between the inlet section 10 and the ultrasonic generator 16, and the measuring device 64 is arranged on the opposite side of the generator 16.

When a blood sample has been introduced into the inlet section 10 it may be moved to the measuring device 63 by the pump P, and the measuring device 63 may now measure the concentration of the electrolyte in the sample of full blood before haemolyzation thereof. Thereafter the sample is moved into the ultrasonic generator 16 where the blood sample is at least partly hemolyzed, and thereafter the pump P may move the haemolyzed sample to the measuring device 64 which measures the electrolyte concentration of the haemolyzed blood sample. On the basis of the signal received from the measuring devices 63 and 64 the computer may calculate and display the data for erythrocyte as well as plasma electrolyte concentrations in the blood sample. Obviously it is possible to provide the apparatus with additional measuring devices for measuring different electrolytes in the same blood sample.

It should be understood that various modifications of the embodiments shown on the drawing may be made without departing from the scope of the appended claims, the most important feature of the invention being that the blood sample introduced in the apparatus is at least partly hemolyzed within the conduit system of the apparatus by means of an ultrasonic generator and that at least one measurement is being made by the apparatus after said hemolyzation.

We claim:

1. An apparatus for hemolyzing a blood sample and for measuring at least one constituent thereof, said apparatus comprising:
   a. a conduit for conducting said blood sample and including a hemolyzing section,
   b. means for generating ultra-sonic waves in walls defining said hemolyzing section so as to at least partly hemolyze a blood sample contained therein,
   c. means for measuring said constituent on the hemolyzed blood sample within said hemolyzing section, and
   d. means for subsequently flushing the blood sample out of said conduit.

2. An apparatus according to claim 1, further comprising an anvil member, a block member, and an ultrasonic generator for vibrating said block member, said hemolyzing conduit section being positioned between and engaged by said anvil member and said block member.

3. An apparatus according to claim 2, further comprising means for resiliently mounting said anvil member.

4. An apparatus according to claim 1, wherein said haemolyzing conduit section comprises transparent wall parts, said measuring means comprising a photometric measuring device including a light source for emitting light through said transparent wall parts and through a blood sample positioned in said hemolyzing conduit section, a photoelectric cell for receiving light having passed through said transparent wall parts, and light filters positionable between said photoelectric cell and said transparent wall parts.

5. An apparatus according to claim 2, wherein said hemolyzing conduit section comprises transparent wall parts, said measuring means comprising a photometric measuring device including a light source for emitting light through said transparent wall parts and through a blood sample positioned in said hemolyzing conduit section, photoelectric cell for receiving light having passed through said transparent wall parts, and light filters positionable between said photoelectric cell and said transparent wall parts.

6. An apparatus according to claim 5, wherein a surface part of said block member engaging said hemolyzing conduit section defines a recess or pocket receiving said photoelectric cell therein, said anvil member having an opening permitting light from said light source to pass therethrough.

7. An apparatus according to claim 5, wherein said hemolyzing conduit section comprises a pair of flat, spaced, transparent panel members of a relatively hard material, and a frame member of a softer material sandwiched between the edge portions of said panel members.

8. An apparatus according to claim 7, wherein said panel members are of glass and said frame member is of hard plastic material.

9. An apparatus according to claim 6, further comprising means for maintaining said hemolyzing conduit section at a substantially constant temperature.

10. An apparatus according to claim 2, wherein said ultra-sonic generator is adapted to generate ultra-sonic waves at a frequency of 15 – 100 kilocycles per second.

11. An apparatus according to claim 4, further comprising electric means for controlling the following operations in timed relationship:
   a. introducing said blood sample into said hemolyzing conduit section,
   b. hemolyzing said blood sample by operating said ultra-sonic generator,
   c. successively positioning at least two different of said light filters between said photoelectric cell and said transparent wall parts, and
   d. flushing said blood sample out of said conduit, and a computer for receiving electrical signals from said photoelectric cell in response to light received by said photoelectric cell from said light source through said filters, and for displaying data for oxygen saturation of said blood sample calculated on the basis of said signals.

12. A method for measuring at least one solute in a sample of whole blood, said method comprising
   a. passing the blood sample into a conduit,
   b. thereafter at least partly hemolyzing said blood sample within a section of said conduit by means of ultra-sound, c. measuring said solute in the hemolyed sample in said conduit section, and d. subsequently flushing said hemolyzed sample out of said conduit.

13. A method according to claim 12, wherein said blood sample is hemolyzed by ultrasound at a frequency of 15 – 100 kilocycles per second.

14. An apparatus for automatically measuring data of blood samples, said apparatus comprising:
   a. a conduit for conducting a blood sample and including a hemolyzing section having transparent wall parts,
   b. means for generating ultra-sonic waves in wall parts defining said hemolyzing section so as to at least partly hemolyze a blood sample contained therein,
   c. a photometric measuring device including a light source for emitting light through said transparent wall parts and through a blood sample positioned therebetween, a photoelectric cell for receiving light having passed through said transparent wall parts and for generating electrical signals in response to the intensity of the light received, and light filters positionable between said photoelectric cell and said transparent wall parts,
   d. means for moving the blood sample into said hemolyzing conduit section and for flushing said sample out of said conduit after hemolyzation and measurement thereof,
   e. electronic control means for controlling the operation of the blood sample moving and flushing means, the ultra-sonic wave generating means, and the photometric measuring device in timed relationship, and
   f. a computer for receiving said signals generated by said photoelectric cell and for transferring them into directly readable digital values.

15. An apparatus according to claim 14, wherein said means for generating ultra-sonic waves comprise an anvil member, a block member, and an ultra-high frequency generator for vibrating said block member, said hemolyzing conduit section being positioned between and engaged by said anvil member and said block member.

16. An apparatus according to claim 15, wherein a surface part of said block member engaging said hemolyzing conduit section defines a recess or pocket receiving said photoelectric cell therein, said anvil member having an opening permitting light from said light source to pass therethrough to said photoelectric cell.

17. An apparatus according to claim 15, wherein said haemolyzing conduit section comprises a pair of flat, spaced, transparent panel members of a relatively hard material, and a frame member of a softer material sandwiched between the edge portions of said panel members.

18. An apparatus according to claim 17, wherein said panel members are of glass, and said frame member is of a hard plastic material.

19. An apparatus according to claim 17, comprising means for maintaining said hemolyzing conduit section at a substantially constant temperature.

20. An apparatus according to claim 19, wherein said frequency generator is adapted to generate ultra-sonic waves at a frequency of 15 – 100 kilocycles per second.

* * * * *